(12) United States Patent
Coakley

(10) Patent No.: US 6,425,530 B1
(45) Date of Patent: Jul. 30, 2002

(54) SCENTED FRESH ROLLS

(76) Inventor: Dan Coakley, 304 Federal Rd., Suite 102, Brookfield, CT (US) 06804-2418

( * ) Notice: Subject to any disclaimer, the term of this patent is extended or adjusted under 35 U.S.C. 154(b) by 0 days.

(21) Appl. No.: 09/606,332

(22) Filed: Jun. 29, 2000

(51) Int. Cl.[7] .................................................. A61L 9/04
(52) U.S. Cl. .......................... 239/52; 239/57; 428/905
(58) Field of Search .......................... 239/52, 57, 34; 428/905; 242/905

(56) References Cited

U.S. PATENT DOCUMENTS

| | | | |
|---|---|---|---|
| 1,552,082 A | | 9/1925 | Riley |
| 2,293,785 A | | 8/1942 | Wintz |
| 2,546,820 A | | 3/1951 | Grant |
| 2,551,418 A | | 5/1951 | Cirigliano |
| 2,639,099 A | | 5/1953 | Gough, Jr. |
| 2,639,939 A | * | 5/1953 | Matchett ................ 239/52 X |
| 2,739,840 A | | 3/1956 | Anderson |
| 2,753,209 A | | 7/1956 | Klasky |
| 2,806,738 A | | 9/1957 | Tsakalas |
| 2,946,511 A | * | 7/1960 | Bartus .......................... 239/52 |
| 2,948,486 A | | 8/1960 | Epeneter |
| 2,988,283 A | * | 6/1961 | Garfield ....................... 239/52 |
| 2,999,642 A | * | 9/1961 | Stone .......................... 239/52 |
| 3,002,704 A | | 10/1961 | Grossfeld |
| 3,017,117 A | | 1/1962 | Klingler |
| 3,329,367 A | | 7/1967 | Paradiso |
| 3,494,505 A | * | 2/1970 | Huebner et al. ........ 428/905 X |
| 4,277,024 A | * | 7/1981 | Spector ..................... 239/56 X |
| 4,759,510 A | | 7/1988 | Singer |
| 4,925,102 A | | 5/1990 | Jones et al. |
| 4,991,538 A | | 2/1991 | Davids et al. |
| 5,071,704 A | * | 12/1991 | Fischel-Ghodsian .... 428/905 X |
| 5,170,938 A | | 12/1992 | Dewing |
| 5,381,984 A | | 1/1995 | Hindsgual |
| 5,494,218 A | | 2/1996 | Armand |
| 5,727,751 A | | 3/1998 | Liu |

FOREIGN PATENT DOCUMENTS

EP 232141 A1 * 8/1987 ................. 428/905

* cited by examiner

*Primary Examiner*—Lesley D. Morris
(74) *Attorney, Agent, or Firm*—St. Onge Steward Johnston & Reens, LLC

(57) ABSTRACT

A paper roll assembly, including a hollow core and a roll of paper which is mounted on the core for mutual rotation therewith, has a fragrance medium affixed to an inner side of the core and covered by an odor impermeable membrane, which is detachable from the fragrance medium during the use of the roll assembly.

25 Claims, 3 Drawing Sheets

SCENTED FRESH ROLLS

FIELD OF THE INVENTION

The present invention relates to dispensing devices and more particularly pertains to a scented element attachable to a surface to eliminate objectionable odors. Specifically, the invention relates to a scented element attachable to an inner surface of a spool before or after a roll of paper has been attached to the spool's outer surface.

BACKGROUND OF THE INVENTION

Air fresheners are a widely used commodity wherever odors are present and there is a conscious need to "freshen" the surrounding air. Typical applications for the air freshener are in a kitchen, restroom or automobile where there is a propensity for odors to accumulate and linger. It is often not practical, as in the winter months, to open a window or operate an air conditioner to clear the air. The common practice, therefore, is to mask or modify the prevailing atmosphere by some sort of air freshener device or aroma generator. The term "aroma" or "fragrance" is not limited to pleasant or savory smells but encompasses scents that function as insecticides, air fresheners, deodorants or any other odor that acts to condition, modify or otherwise charge the atmosphere. Thus, the effect of the air freshener is to emit a selected fragrance scent that serves to dispel or neutralize the offensive effects of the odors, which are otherwise present to at least enhance the apparent quality of air thereabout.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

Over the years many devices have been on the market. Some of these devices try to exhaust the odors out of the room after they have escaped from the toilet bowl and others try to cover up the objectionable odors with strong perfumed scents.

Typically, the air freshener composition is in a liquid, powder or gel form from which the scent dispensed by various means such as an exposed air wick, gravity air circulation through an open canister, a manually actuated aerosol, etc., as are well known in the art. The disadvantage of aroma generators in which the fragrance is stored in a porous member is that the fragrance is slow to volatilize. Numerous attempts undertaken to overcome the disadvantage of aroma generators are well illustrated in the following patents.

U.S. Pat. No. 5,170,938 to Dewing discloses a paper roll holder with a scented material carried by a support disk member. The disk member periodically needs to be replaced which may be difficult for an inexperienced user; also, a cost of the paper roll holder provided with the disk member may be unjustifiably high.

U.S. Pat. No. 5,294,218 to Armand discloses a paper holder including a cylinder which is made of resilient material allowing a scent to escape from the cylinder through its opposite perforated ends upon applying an external force. A user may be required to apply a significant force to the cylinder that sometimes is difficult to achieve for elderly people or children. Further, a cost of the paper holder made of resilient material and having perforated ends may be prohibitively high.

U.S. Pat. No. 2,293,785 to Wintz discloses a paper roll assembly having a hollow cylinder of deodorizing material, which is cast or molded to an inner surface of a cardboard tube carrying a roll of paper upon its outer surface. One of the disadvantages this structure may have is the impossibility of replacing the deodorizing cylinder when it stops being effective but before the roll of paper is used up. Still another disadvantage may be a prohibitive cost of production of a multilayer structure, as disclosed in this patent.

All of the above disclosed structures of the scented paper roll assembly continually give off a scent before the paper roll is installed in a bathroom, thus decreasing efficiency of its performance.

It is, therefore, desirable to provide a scented article that can be manufactured separately from a paper roll and easily mounted on a surface of a support core carrying the paper roll at the time the paper roll is installed for its direct use. A scented article having a simple structure allowing a user to easily replace it after the current scented article lost its efficiency is also desirable, as is a scented article that can invariably fit different inner diameters of paper rolls.

SUMMARY OF THE INVENTION

In view of the foregoing disadvantages, the present invention provides a new scented article that does not allow the fragrance to bleed off into a paper product or air by virtue of a hermetically sealed membrane exposing the fragrance upon its detachment at the time the product is used.

According to one aspect of the invention, a scented article sticker is comprised of a flat layer of substrate carrying a layer of fragrance disposed on one side of the substrate, which also carries a layer of adhesive on its opposite side. A scented impermeable membrane attached to both the fragrance and the adhesive is easily peeled away allowing, thus, the substrate to be glued to an inner surface of a core of the paper product. Unwinding of the paper product causes the fragrance particle grains to be broken necessitating the scent to be re-released.

In accordance with another aspect of the invention, an odor impermeable membrane covers only a fragrance layer disposed on one side of a substrate, whereas its opposite side is impregnated with an adhesive medium becoming effective upon applying external causes, such as moisturizing, heating or pressing. Thus, the membrane can be removed after the substrate has been adhered to the inner surface of the core of a paper product.

Still a further aspect of the invention relates to a tubular substrate made of resilient material and covered on its inner side with the fragrance that, in turn, is protected by a detachable scent-impermeable membrane. Because of the resilience of the substrate, its outer diameter may be slightly larger than an inner diameter of the core in a rest position, wherein no external forces act thereupon. However, once acted upon, a scented article can be introduced into the core, and after the force has been seized it expands pressing upon the core. The substrate can be selected from a group consisting of polymeric materials, steel etc. If the substrate is made of metal, then, in accordance with a sub-aspect of the invention, the tubular scented articles provided with an axial recess allowing the user to squeeze it in order to reduce the scent's diameter.

It is therefore an object of this invention to provide a scented assembly having a fragrance layer that does not bleed off before it is attached to a paper roll.

Still a further object of the present invention is to provide a flat scented assembly comprised of a flat substrate sandwiched between an adhesive and fragrance layer and wrapped in an easily detachable scent impermeable membrane.

Another object of the invention is to provide a scented assembly having a substrate sandwiched between an adhesive and fragrance layer, wherein only the fragrance layer is detachably attached to a peel away membrane.

Still another object of the invention is to provide a tubular scented assembly having a three layer concentric structure preventing a fragrance layer from bleeding off before an outer adhesive layer is attached to a paper product.

Yet a further object is to provide a tubular scented assembly made of resilient material to fit differently dimensioned tubes, cores and paper products.

BRIEF DESCRIPTION OF THE DRAWINGS

The above and other objects, features and advantages will become more readily apparent from the following description accompanied by the following drawings, in which.

DETAILED DESCRIPTION OF THE DRAWINGS

Referring to FIGS. 1–4, a multi-layer scented assembly 10 that can be purchased either separately from a paper roll or attached to an inner surface of core carrying the paper roll during a manufacturing stage, includes a basic structure comprised of a substrate layer 14 which is interposed between an adhesive layer 16 and a fragrance layer 12.

Figure 4:
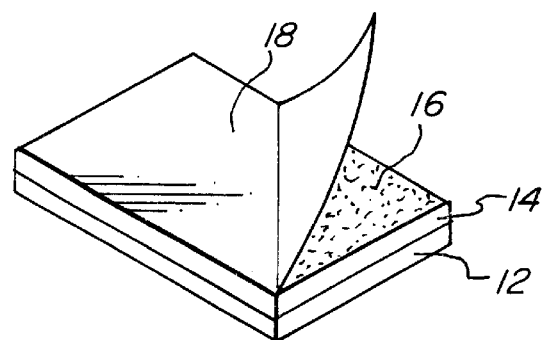
FIG. 4 is an exploded isometric view of a scented assembly in accordance with the another embodiment of the invention.

The scented assembly 10, if manufactured separately from a paper roll, further includes a membrane 18 detachably attached to the opposite sides of the scented assembly 10, thus covering the adhesive layer 16 and the fragrance layer 12, as better seen in FIG. 4. The membrane is hermetically sealed to preserve the fragrance before the scented assembly attached to the paper roll is ready to be used. Alternatively, the membrane 18 can be attached only to the fragrance layer if the scented assembly is attached to the inner surface of the hollow core during a manufacturing stage of the paper roll.

Numerous types of adhesives can be utilized to detachably attach the membrane to both the fragrance and substrate layer. For example, a group of adhesives selected from thermosetting, pressure sensitive, film and hot melt adhesives is given here only by way of example and can be vastly expanded as long as an adhesive can meet the requirements of the present invention.

Similarly to the adhesive layer, the membrane 18, required to preserve the fragrance from bleeding off in the air before the use of the paper roll, can be selected from a wide range of materials. A material preventing moisture or air from transferring through its surface and selected from the group consisting of synthetic fiber, such as styrene latex and polyester synthetic fiber, nylon, rubber, Mylar or plastic films and even tightly woven natural fabric can be used.

Unlimited number of substrates basically required to be relatively flexible to adhere to a curved surface can be selected from a wide variety of materials including different fabrics and polymeric materials. Selection of the components of the scented assembly also has to be such that if it is manufactured as a flat strip, its thickness should not exceed a maximum of a few millimeters. The fragrance layer can include a plurality of fragrance pallets or be in powder form or any other known selected perfume base having a pleasant odor which permeates the surrounding area.

To activate the scented assembly, a user initially peels away the membrane 18 from the adhesive layer to attach the scented assembly to the inner surface of the core 20 (FIG. 2) carrying a paper roll 22, and then detaches the membrane 18 from the fragrance layer 12. Thus, after mounting a paper roll assembly with the attached scented assembly to a spindle or support 24 (FIG. 2), the fragrance layer gives off the scent generated every time when a paper roll unwinds causing the fragrance grains to brake.

Figure 1:
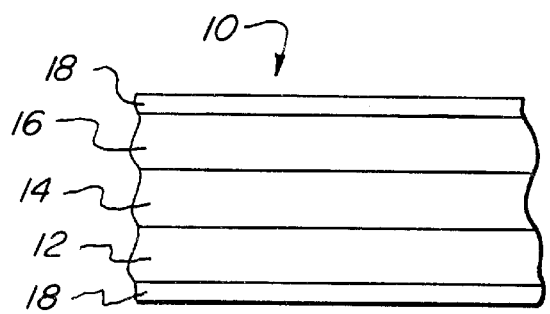
FIG. 1 is a diagrammatic view of a scented assembly in accordance with the invention.
Figure 2:
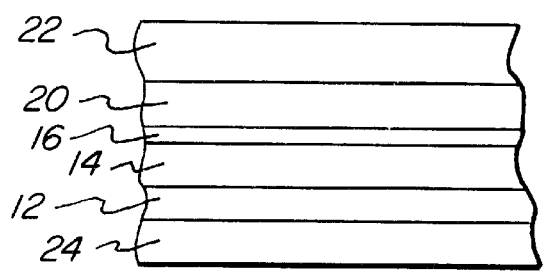
FIG. 2 is a cross-sectional view of a paper roll assembly shown with the scented assembly of FIG. 1.
Figure 3:
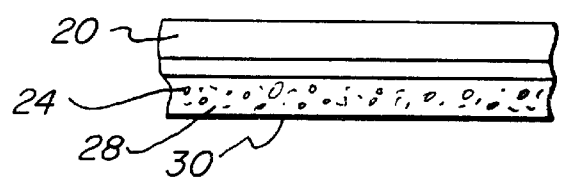
FIG. 3A is an exploded view of the scented assembly of FIG. 1

According to another aspect of the invention, as shown in FIG. 3, the fragrance grains 28 can be directly impregnated in the substrate layer 14 which has a form of strip covered by the adhesive layer 16 and the membrane 18. The scented assembly, as shown in FIG. 3, is easy to prepare which, in turn, leads to a cost efficient process of preparing the assembly 10. Adherence of the scented assembly to the inner surface of the core 20 of the paper roll assembly is similar to the one described above and includes pulling a membrane from at least one of the opposite sides of the scented assembly. If the scented assembly is attached to the inner surface of the core 20 during manufacturing of a paper roll assembly, then, of course, the membrane covers only an outer side 30 of the scented assembly facing away from the inner surface of the core.

Figure 5:
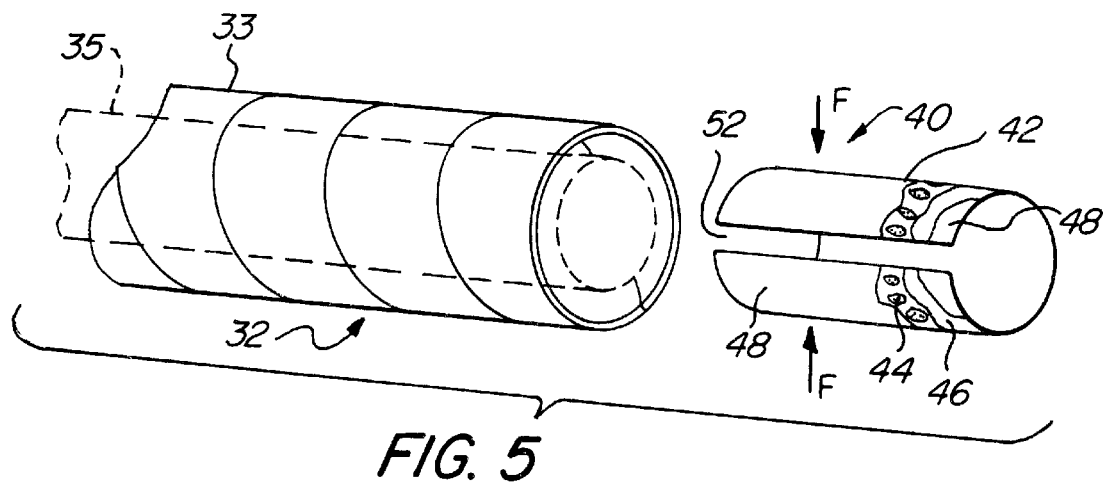
FIG. 5 is a longitudinal cross sectional view of still another embodiment of a scented assembly having a substrate layer formed as a container.

Referring to FIG. 5, a scented assembly 40 includes a tubular substrate 42 shaped and sized to be inserted between a core 32 of a paper roll assembly carrying a paper roll on its outer surface 33 and a roll holder support 35 illustrated in dash lines. In accordance with the main concept of the invention, the substrate 42 has a fragrance layer 46 on its inner side and an adhesive layer 44 on its outer side. Completing the scented assembly is at least one membrane 48 detachably covering the fragrance layer provided that the scented assembly is manufactured with the paper roll. If the scented assembly is replaceable, than two membranes 48 cover the adhesive and fragrance layers, respectively. As the paper roll assembly rotates an outer surface of the support 35 engages the fragrance layer 46 to generate the scent and reexecute the fragrance by rubbing against the core roll support.

Preferably, the substrate 42 has an elongated recess 52 providing the substrate with a degree of flexibility. As a consequence, if the scented assembly 40 is manufactured separately from the paper roll assembly, its diameter may exceed an inner diameter of the core 32 in order to fit differently sized paper roll assemblies, such as toilet paper and paper towel rolls. Upon applying an external force F, as indicated by arrows, a user can easily insert the scented assembly into the core, and after ceasing of the force, the scented assembly tends to expand pressing upon the inner surface of the core. Having the resilient structure, as described above, it is possible to dispense with an adhesive layer since an outwardly directed resilient force, which is inherent in the scented article assembly, is sufficient to provide reliable contact between the core and the scented article assembly. The substrate can be made of a variety of materials including, for example, plastic or cardboard. At the time of installment of the scented assembly a user peels away the membrane covering the fragrance layer, as shown in FIG. 4 and attaches the assembly 40 to the inner surface of the core 32.

Figure 6:
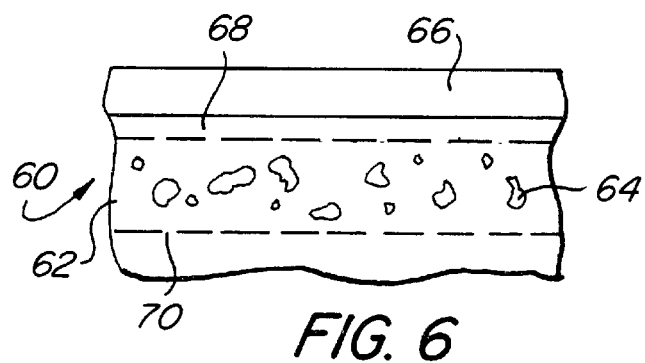
FIG. 6 depicts a diagrammatic view of the scented assembly in FIG. 1 with a plurality of fragrance pallets.

Turning to FIG. 6, a scented assembly 60 includes a substrate formed as a container 62 which is filled with a plurality of fragrance pallets 64 particles of which are given off and disseminated in the atmosphere during rotation of a paper roll assembly to which the container is attached. Similarly to the previously described embodiments of the present invention, the container 62 is covered by an adhesive layer 68 interposed with a detachable membrane 66 which is removed from the container at the time of installment of the scented article assembly. A periphery of the container is perforated to have a plurality of holes 70 each sized to prevent an individual pallet from escaping the interior of the container but allowing small broken particles of the pallets to egress upon using of the paper roll assembly.

Figure 7:
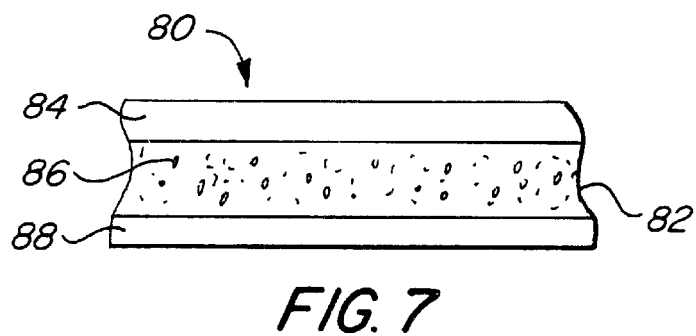
FIG. 7 depicts another embodiment of the scented assembly of FIG. 1 having a core impregnated with a fragrance substance during manufacturing.

FIG. 7 illustrates a simplified embodiment of a scented roll assembly 80 comprised of a core 82 which is impregnated with a fragrance substance 86 during manufacturing of the assembly that further includes a roll of paper 84 on the outer side of the core. A detachable membrane 88 adhered to the inner side of the core 82 prevents premature dissemination of the fragrance in the atmosphere, similarly to the previously described embodiments.

Figure 8:
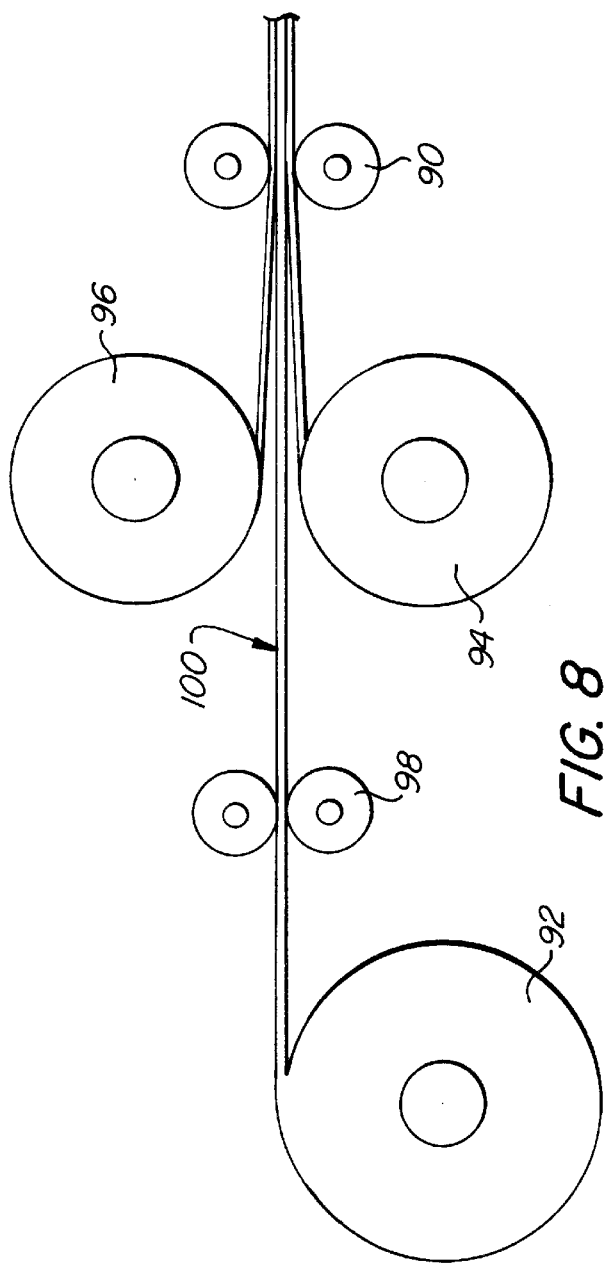
FIG. 8 depicts a process for manufacturing the assembly of FIG. 1.

A process of manufacturing of a paper roll assembly carrying a scented assembly, in accordance with the invention, does not require substantial modification of the known industrial processes. As diagrammatically shown in FIG. 8, a roll of fragrance layer 92 is advanced along a transport path 100, a downstream stretch of which has at least two rolls 94 and 96 juxtaposed with one another to supply the membrane and substrate layers, respectively. Pair of pressure rolls 90 activate adhesive, such as pressure sensitive adhesive applied at 98. It is easy to see that many of the processes known in the paper-roll industry do no have to undergo serious changes in order to be employed in manufacturing the scented assembly in accordance with the present invention.

Figure 9:
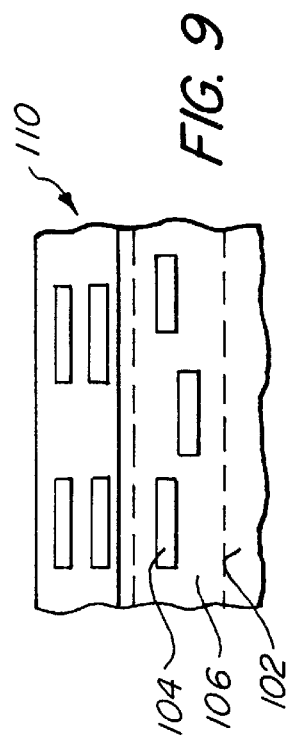
FIG. 9 depicts a kit of several scented assemblies.

In the embodiments of the invention including a scented assembly manufactured separately from a paper roll, it is advantages to manufacture a kit 110 including several scented assemblies. A variety of different patterns in which the assemblies can be arranged are foreseeable within the context of this invention including a circular or matrix-like pattern or a pattern wherein strips of adjacent rows overlap one another, as illustrated in FIG. 9. The kit 110 has a base 102 with a plurality of scented strips 104, each including a substrate which is glued to the base and impregnated with a fragrance medium. Covering each of the scented strips is a membrane layer 106, as shown in dash lines, which is easily detachable by a user at the time of attachment of a scented strip to a roll assembly. Alternatively, if the scented strips can be arranged in the overlapping pattern, then a single membrane exposing one strip at a time can be used to prevent the rest of strips from being prematurely exposed.

It is also conceivable within the scope of the invention to have the paper roll coated with fragrance. During rotation of the paper roll scent will be emitted in the ambient atmosphere due to the friction of adjacent layers of paper.

Note that the optimum dimensional relationships for the scented assembly including variations in size, shape, materials, form and manner of operation, as illustrated in the drawings and described hereinabove, can vary without, however, departing from the scope of this invention.

Therefore, the foregoing is considered only as illustrative of the principles of the invention, as defined by the appended claims.

What is claimed is:

1. A scented paper roll assembly for use with a spindle of a toilet paper dispenser, comprising:
   a cylindrical core of a toilet paper roll having an inner surface, said inner surface surrounding the spindle;
   a flexible substrate removably inserted between said inner surface of said core and the spindle, said substrate having a first side and a second side;
   an adhesive medium affixed to at least one of said first and second sides for attaching said substrate to said inner surface of said core;
   a fragrance medium affixed at least to one of said first and second sides; and
   a peel-away odor-impermeable membrane detachably attached to said fragrance medium on a side of said fragrance medium opposite from said inner surface, said membrane being removed from said fragrance medium when it is desired for said substrate to allow said fragrance medium to release scent during rotation of said paper roll as said fragrance medium is continuously agitated upon contact between the spindle and said inner surface;
   wherein said membrane is a pliable sheet.

2. The roll assembly defined in claim 1 further comprising another peel-away membrane for covering said adhesive medium prior to use.

3. The roll assembly defined in claim 1 wherein said substrate is a flexible strip.

4. The roll assembly defined in claim 3 wherein said flexible substrate has an endless annular periphery.

5. The roll assembly defined in claim 3 wherein said flexible substrate is made of resilient material and has an annular periphery extending along a longitudinal center axis, the annular periphery having an axial recess extending between opposite ends of said flexible substrate to allow said substrate to be inserted into said core of the paper roll.

6. The roll assembly defined in claim 1 wherein said adhesive medium is selected from the group consisting of thermosetting, pressure sensitive and film adhesive.

7. The roll assembly defined in claim 1 wherein said substrate is selected from the group consisting of polymeric, fabric and cardboard material.

8. An air freshener comprising:
   a cylindrical core of a toilet paper roll having an outer surface and an inner surface, said inner surface surrounding the spindle;
   a flexible substrate removably inserted between said inner surface of said core and the spindle, said substrate being attachable to said inner surface;
   a fragrance medium impregnated in said flexible substrate; and a membrane detachably attached to said substrate to prevent said fragrance medium from deodorizing the atmosphere before said membrane is removed;

wherein said membrane is a pliable sheet.

9. The air freshener defined in claim 8 wherein said flexible substrate has a tubular shape.

10. The air freshener defined in claim 8 wherein said flexible substrate is a flat strip.

11. The air freshener defined in claim 8 further comprising an adhesive medium affixed to a side of said substrate opposite to said membrane.

12. The air freshener defined in claim 9 wherein said flexible substrate has an elongated recess and is made of a resilient material.

13. A replacement set comprising:

a cylindrical core of a toilet paper roll having an inner surface, said inner surface surrounding the spindle;

at least one odor impermeable membrane detachably connected to said core;

wherein said membrane is a pliable sheet; and a plurality of flexible substrates between said core and said at least one membrane, each of said substrates being impregnated with a fragrance medium prevented from deodorizing the atmosphere by said at least one membrane and being removable from said core upon pulling said at least one membrane away.

14. The replacement set defined in claim 13 wherein said at least one odor impermeable membrane includes a plurality of separate segments each covering a respective one of said plurality of flexible substrates arranged in a honeycomb pattern.

15. A paper roll assembly comprising:

a core of a toilet paper roll having an inner and outer periphery;

a container attached to the inner periphery of said core and having a peripheral wall defining an inner space;

a plurality of thoroughgoing openings formed on a region of the peripheral wall, said plurality of openings sized for homogeneous, steady emission of fragrance;

a plurality of fragrance pallets in said inner space, each of said openings being sized to prevent egress of the entire pallet from the space; and a detachable membrane hermetically closing the region of the peripheral wall, the pallets breaking down into a plurality of particles upon rotation of the roll to escape the inner space from said plurality of openings after said membrane has been removed from the region;

wherein said membrane is a pliable sheet.

16. A process for preparing a scented roll comprising the steps of:

forming a core having an inner and outer surface;

forming a roll of paper on the outer side of the core;

affixing a fragrance medium to the inner surface of the core;

detachably attaching an odor impermeable membrane to the fragrance medium to prevent deodorizing of the atmosphere before peeling it away.

17. The process defined in claim 16 wherein the fragrance medium is attached to the core before forming the roll of paper.

18. The process defied in claim 16 wherein the fragrance medium is attached to the core after forming the roll of paper.

19. The process defined in claim 16 further comprising the step of affixing a flexible substrate to the inner surface of the core, said fragrance medium being coated upon the substrate.

20. The process defined in claim 19 wherein said substrate is provided with an adhesive layer.

21. The process defined in claim 19 wherein said substrate is tubular and made of a resilient material, the process further comprising the step of longitudinally recessing the tubular substrate.

22. A process for preparing a scented roll comprising the steps of:

forming a core of a toilet paper roll having an inner and outer surface;

coating a plurality of paper layers detachably attached to one another with a fragrance medium;

covering the fragrance medium with a detachable membrane layer;

forming a roll of the paper layers; and releasing fragrance medium upon frictionally detaching paper layers from one another during unwinding the paper roll.

23. A method for activating a scented roll assembly, comprising:

providing a flexible substrate having a first side and a second side, depositing a fragrance medium on the first side for providing a scent;

depositing an adhesive on the second side for providing a securing mechanism;

adhering the substrate to an inner diameter of a roll of paper by pressing the adhesive to the inner diameter;

mounting the roll of paper to a spindle;

removing a detachable odor impermeable membrane from the fragrance medium; and scraping the fragrance medium to activate the scented roll assembly by rotating the roll of paper about the spindle.

24. The method according to claim 23, wherein the roll of paper is toilet paper.

25. The method according to claim 23, further comprising the step of attaching an odor impermeable membrane to the fragrance medium to impede an escape of fragrances.

* * * * *